United States Patent [19]

van Wersch et al.

[11] 4,199,573

[45] Apr. 22, 1980

[54] DIAZABORINES AND DRUG COMPOSITIONS

[75] Inventors: Hubert M. A. van Wersch, Kerkrade, Netherlands; Siegfried Herrling, Stolberg; Heinrich Mückter, Aachen, both of Fed. Rep. of Germany

[73] Assignee: Grünenthal GmbH, Stolberg, Fed. Rep. of Germany

[21] Appl. No.: 928,589

[22] Filed: Jul. 27, 1978

Related U.S. Application Data

[63] Continuation-in-part of Ser. No. 708,361, Jul. 26, 1976, Pat. No. 4,112,077.

[30] Foreign Application Priority Data

Mar. 15, 1978 [DE] Fed. Rep. of Germany ....... 2811132

[51] Int. Cl.$^2$ ..................... A61K 31/69; A61L 13/00; A61L 23/00; C07F 5/02
[52] U.S. Cl. ................................. 424/185; 260/502.3
[58] Field of Search ...................... 260/502.3; 424/185

[56] References Cited

U.S. PATENT DOCUMENTS

| | | | |
|---|---|---|---|
| 3,714,206 | 1/1973 | Huemer et al. | 260/502.3 X |
| 4,112,077 | 9/1978 | van Wersch et al. | 260/502.3 |

*Primary Examiner*—Helen M. S. Sneed
*Attorney, Agent, or Firm*—Weiser, Stapler & Spivak

[57] ABSTRACT

Derivative of 1-hydroxy-benzo-2,3,1-diazaborines which are substituted in the 2-position by a sulfo group linked to a defined aliphatic radical like alkyl or alkenyl and which may be substituted on the benzene ring by one or more lower alkyl radicals and/or halogen atoms and salts of such compounds. The pharmaceutical compositions containing these diazaborines are highly effective against gram-negative bacteria. The new compounds are prepared by reacting o-formyl phenyl boric acid, which may be substituted, with the respective aliphatic sulfonic acid hydrazide or by reacting the respective (substituted) benzaldehyde sulfonylhydrazone with a boron trihalogenide.

30 Claims, No Drawings

DIAZABORINES AND DRUG COMPOSITIONS

The present application is a continuation-in-part of allowed and pending application Ser. No. 708,361, filed July 26, 1976 and entitled "Diazaborines and Drug Compositions" which issued on Sept. 5, 1978, as U.S. Pat. No. 4,112,077.

The invention relates to new derivatives of 1-hydroxybenzo-2,3,1-diazaborine, a process for their preparation, and therapeutic compositions. The compositions of the invention are especially effective antibacterial compositions against gram-negative bacteria. In U.S. Pat. No. 3,714,206, of Jan. 30, 1973, to Huemer et al, entitled BENZO-2,3,1-DIAZABORINES and in British Patent Specifications Nos. 1,182,132 and 1,202,219 (and corresponding patents in other countries), there are disclosed 1-hydroxy-2,3,1-diazaborine derivatives which are linked in the 5,6-position to a phenylene-, thienylene- or naphthylene ring and which are substituted in the 2-position with a sulfo group linked to an unsubstituted or, preferably, substituted aromatic or heterocyclic radical. These compounds are useful antimicrobial agents and are especially effective against gram-negative bacteria. Preferred members of the known group of substances are derivatives of 1-hydroxy-benzo-2,3,1-diazaborines.

Although 2-arylsulfonyl substituted 2,3,1-diazaborine derivatives have been known for several years, there is no disclosure of 1-hydroxy-sulfonyl-benzo-2,3,1-diazaborines, which are 2-alkyl-substituted, and which are antibacterially active.

A new class of derivatives of 1-hydroxy-benzo-2,3,1-diazaborines has now been discovered, the members of which are, unexpectedly, useful as antimicrobial agents. The class of compounds of the invention is represented by the general formula

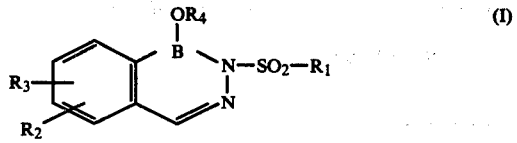

wherein
R₁ is acyclic alkyl or alkenyl which may be branched or straight, has 2 to 5 carbon atoms and which may be substituted by 1 to 3 halogen atoms, preferably chlorine atoms, or R₁ represents a mono-, di- or tri-halogen methyl radical, R₂ and R₃ are the same or different and are selected from the group consisting of hydrogen, C₁ to C₄ alkyl, or a fluorine, chlorine or bromine atom and R₄ is a hydrogen atom or a pharmaceutically acceptable cation, preferably an alkali metal cation.

In preferred compounds of the class, R₁ may have 3 to 4 carbon atoms or may have 1 to 3 carbons being substituted by 1 to 3 halogen atoms, preferably chlorine. R₁ may also advantageously be an alkenyl such as allyl, vinyl or crotyl. Preferred members also include those where R₁ is a mono-, di- or tri-halo-substituted methyl or ethyl radical. Preferred members of the class of chloro-substituted R₁ constituents are those where R₁ is chloromethyl, monochloro-substituted, or dichloropropyl.

In a preferred group of compounds one of R₂ and R₃ represents hydrogen and the other is attached to position 6 of the ring system, the other of the radicals R₂ or R₃ representing a methyl- or an ethyl group or a fluorine atom.

For a better appreciation of the subject matter of this invention, it should be kept in mind that while gram-positive pathogens were an important cause of bacterial infections in mammals in the 1950's, gram-negative bacteria have become an increasingly important and pernicious cause of infections during the last decade. Several studies have shown that a large proportion of bacterial infections in United States hospitals are induced by gram-negative pathogens.

While it is recognized that there is an adequate supply of chemo-therapeutic drugs available for the control of gram-positive bacteria, that drugs effective in the control of gram-negative bacteria leave very much to be desired. While the benzo-2,3,1-diazaborines of U.S. Pat. No. 3,714,206 are a significant contribution to the pharmaceutical and medical arts in human and veterinary therapy it has been quite unexpected to find another class of boron containing heterocyclic compounds specifically substituted in the 2-position as defined herein, which are so effective against gram-negative bacteria, in particular *E. coli*. Furthermore, the antimicrobial compounds of the invention unexpectedly differ in their low toxicity and effectiveness when compared to compounds structurally analogous or homologous.

The new compounds of formula I have pronounced controlling activity against microorganisms. This activity has been demonstrated not only in vitro but also in effected animals on parenteral or oral administration of the compounds, this in accordance with standard test methods adapted and recognized by those skilled in the art as being properly correlated with human utility.

The compounds of the invention are effective in controlling gram-negative bacteria such as *Escherichia coli*, *Salmonella typhimurium*, *Proteus vulgaris*, *Proteus mirabilis*, and others.

The compounds of the invention are administered in an amount effective to control the gram-negative bacteria and less than the amount which is toxic to the subject treated. A convenient therapeutic daily dose is in the range of about 250 to about 1500 mg. Smaller dosage cause generally a slower control of the bacteria.

Typical of the compounds of the class are very active antimicrobial agents, especially against gram-negative bacteria, in particular *E. coli*. For instance, the following values of the CD₅₀ were determined on administering the listed compounds of formula I, in which R₁ is as defined in the following Table I, Antimicrobial Activity, R₂ and R₃ are hydrogen and wherein R₄ is sodium to mice infected with the bacteria shown.

Table I

| | ANTIMICROBIAL ACTIVITY | |
|---|---|---|
| | | *E. coli* (CD 50 mg/kg) |
| | R₁ | p.o. | s.c. |
| 1 | C₂H₅— | 11.0 | 9.8 |
| 2 | n-C₃H₇ | 7.0 | 6.7 |
| 3 | i-C₃H₇— | 12.5 | 9.2 |
| 4 | n-C₄H₉— | 11.2 | 5.85 |
| 5 | CH₃\CH—CH₂—/CH₃ | 8.85 | 10.6 |
| 6 | CH₂=CH—CH₂— | 13.2 | 13.2 |
| 7 | Cl—CH₂— | 12.4 | 11.8 |
| 8 | CH₃—CH(Cl)— | 17.7 | 14.8 |

Table I-continued

| | ANTIMICROBIAL ACTIVITY | |
|---|---|---|
| | | E. coli (CD 50 mg/kg) |
| | $R_1$ | p.o. s.c. |
| 9 | $Cl-CH_2-CH_2-CH_2-$ | 22.7  21.8 |

$CD_{50}$ = Dose in mg of compound/kg of mouse body weight which cures the infection in 50% of the animals The compounds of the invention also show effectiveness against other gram-negative bacteria. For instance, the $CD_{50}$-values for compound 2 ($R_1=nC_3H_7-$) against B. proteus are 18.7 mg/kg under per oral ("p.o.") administration and 11.7 mg/kg under subcutaneous ("s.c.") administration and against Klebsiella pneumoniae 11.3 mg/kg p.o. and 6.75 mg/kg s.c.

Table II shows $CD_{50}$-values for the compound of formula I, in which $R_1$ is 3'-chloro-n-propyl-, $R_2$ is 6-methyl, $R_3$ is hydrogen and $R_4$ is sodium (compound 10) and for the compound in which $R_1$ is n-propyl-, $R_2$ is 6-fluoro, $R_3$ is hydrogen and $R_4$ is sodium (compound 11) determined in mice infected with the bacteria shown:

Table II

| | ANTIMICROBIAL ACTIVITY | | | |
|---|---|---|---|---|
| | $DC_{50}$ (mg/kg) on administering | | | |
| | Compound 10 | | Compound 11 | |
| Germ | p.o. | s.c. | p.o. | s.c. |
| E. coli | 9.8 | 8.8 | 6.95 | 5.65 |
| Proteus mirabilis | 9.15 | 7.45 | 13.9 | 7.45 |
| Proteus vulgaris | 8.6 | 8.4 | 13.9 | 7.45 |
| Klebsiella aeruginosa | 9.15 | 6.95 | 5.65 | 4.25 |

Table III, Minimum Inhibitory Concentration "MIC," shows the concentration in μg/ml of various compounds of formula I (wherein in each case $R_3$ is hydrogen, $R_4$ is sodium and $R_2$ if different from hydrogen is attached to the 6-position) which inhibit the growth of the bacteria mentioned.

Table III

| | | MINIMUM INHIBITORY CONCENTRATION | | | | |
|---|---|---|---|---|---|---|
| $R_1$ | $R_2$ | E. coli | Proteus mirabilis | Proteus vulgaris | Klebsiella aeruginosa | S. typhi murium |
| $-CH_2-CH_2-CH_3$ | H | 4 | 32 | 32 | 8 | 16 |
| $-(CH_2)_4-CH_3$ | H | 32 | 32 | 32 | 8 | 16 |
| $-CH_2-CH-CH_3$ \| $CH_3$ | H | 8 | 16 | 16 | 4 | 4 |
| $-CH_2-CH_2-CH_3$ | F | 4 | 4 | 4 | 8 | 8 |
| $-CH_2-CH_2-CH_3$ | $C_2H_5$ | 4 | 8 | 2 | 1 | 2 |
| $-CH_2-CH-CH_3$ \| $CH_3$ | $CH_3$ | 2 | 8 | 4 | 2 | 8 |
| $-CH_2-CH_2-CH_2Cl$ | F | 16 | 16 | 8 | 8 | 4 |
| $-CH_2-CH_2-CH_2-Cl$ | $CH_3$ | 2 | 4 | 4 | 1 | 1 |
| $-CH_2-CH_2-CH_2-Cl$ | $C_2H_5$ | 4 | 2 | 4 | 2 | 2 |

It is noteworthy that the $-CH_3$ and the higher alkyl ($R_1$) analogs are inadequately effective in the control of the bacteria. For comparison, also, the compound of Example 58 of U.S. Pat. No. 3,714,206, 1-hydroxy-2(2'-chloro-4'-amino-phenyl sulfonyl) benzo-2,3,1-diazaborine, has the following effectiveness, as shown in Table IV.

Table IV

| | COMPARATIVE ANTIMICROBIAL ACTIVITY | |
|---|---|---|
| | E. coli | ($CD_{50}$ mg/kg) |
| $R_1$ | p.o. | s.c. |
| $CH_3-$ | 100 | 100 |
| $n-C_6H_{13}-$ | 100 | 42.3 (toxic) |
| $n-C_8H_{17}-$ | >1600 | 400 (toxic) |
| $n-C_{12}H_{25}-$ | >1600 | >1600 |
| 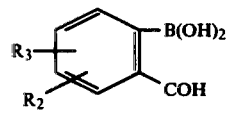 | 36 | 13.5 |

It is apparent that the class of compounds of the invention is highly effective in the control of gram-negative bacteria. In the compounds of the invention, it is preferred that $R_1$ in formula I contain only one halogen atom, especially one chlorine atom.

Where $R_1$ is alkenyl of more than 2 carbon atoms, the double bond therein can be positioned between any two of the carbon atoms. It is, however, preferred that the double bond be positioned between carbon atoms 2 and 3 in the alkenyl group.

The compounds of the invention are prepared by condensing an o-formyl phenyl boric acid derivative of formula II

wherein $R_2$ and $R_3$ have the same meaning as defined above with a sulfonic acid hydrazide of formula III $$H_2N-NH-SO_2-R_1 \qquad (III)$$

wherein $R_1$ has the same definition as above. In the resulting product $R_4$ represents hydrogen. This compound can be converted to its corresponding salts, in which $R_4$ is a pharmaceutically acceptable cation.

As many of the compounds of formula III are relatively unstable, it is advisable to prepare them, for instance, by reacting the corresponding sulfonic acid chloride with hydrazine hydrate and introduce them directly, without purification, as crude products into the process of the invention, and then proceed as described.

Preferably the sulfonic acid hydrazide of formula III is reacted with the o-formyl-phenyl boric acid derivative of formula II in the presence of a solvent or a suspending diluent, such as an alkanol, dioxane, tetrahydrofurane, an aromatic hydrocarbon, for instance benzene or toluene, and if required at elevated temperature.

For further details about this method of preparation of the compounds of the invention, including conditions and reactants, reference is made to U.S. Pat. No. 3,714,206 which is incorporated herein by reference for convenience to one skilled in the art.

Compounds of formula I in which $R_1$ represents a haloalkyl radical containing 2 to 5 carbon atoms and 1 to 2 halogen atoms may also be prepared by adding a halogen or a hydrogen halide to the double bond in the alkenyl group of a compound of formula I in which $R_1$ represents an alkenyl group containing 2 to 5 carbon atoms and in which $R_4$ is hydrogen.

In this reaction the alkenyl group containing starting material is dissolved, for instance, in glacial acetic acid or in a halo-alkane such as chloroform or dichloro methane and treated—preferably while illuminating—with the halogen, for instance, chlorine or bromine, until the double bond is saturated. Especially in case of adding a hydrogen halide such as hydrogen chloride or hydrogen bromide, it is advisable to heat the reaction mixture in order to speed up the reaction, such as in a temperature range of 30° C. to 80° C.

The compounds of the invention may also be prepared by reacting a compound of formula IV

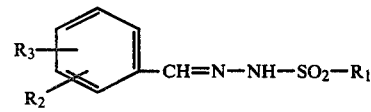

IV wherein $R_1$ to $R_3$ are as defined above with a boron trihalogenide and hydrolyzing the first product of the reaction to liberate the 1-hydroxy group. This reaction is preferably made in presence of a polar solvent or diluent expecially in presence of a halogenated hydrocarbon. Solvents which may be used are such as dichloro methane, chloroform, carbon tetrachloride or such as hexane, cyclohexane, benzene, toluene, chloro benzene and other commonly used solvents.

The boron trihalogenide is preferably boron tribromide but there may be used also boron trichloride or boron tri iodide.

The reaction may be performed in a temperature range from about room temperature to about 100° C. Preferably moderately elevated temperatures of about 40° to 80° C. are used.

If desired, the reaction may be faciliated by adding a catalyst having a favorable influence on the ring closing step of the reaction such as an excess of the boron trihalogenide or metal halogenides, for instance aluminum chloride, tin chloride, zinc chloride or iron chloride.

The compounds of formula IV may easily be prepared by reacting a benzaldehyde of formula V

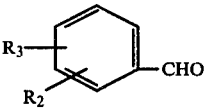

V wherein $R_2$ and $R_3$ have the same meaning as above with a sulfonic acid hydrazide of formula III.

The compounds of formula IV need not to be isolated. It is also possible to react compounds V and III and to treat the reaction mixture directly (preferably after elimination of the water formed in the reaction) with the boron trihalogenide.

Due to the hydroxyl group linked to the boron atom, the compounds of formula I, wherein $R_4$ is hydrogen, are capable of forming salts with bases, in which salts $R_4$ is a cation. For instance, solutions of such salts can be prepared in that a compound of formula I can be shaken with dilute (e.g., 0.1 to about 2 normal) sodium or potassium hydroxide, aqueous ammonia solutions or with solutions of organic bases, such as triethylamine, ethylene diamine, diethanol amine and so on. Especially the alkali salts may be easily isolated from such solutions, for instance by freeze drying. When organic solutions are used, they are conveniently 5 to 10% solutions.

Since the compounds of the invention exhibit only low toxicity, they are very well suited for therapy or control of gram-negative infections in man and in animals. They can be administered orally, parenterally, topically or rectally.

The following examples are merely illustrative of the invention; they are not to be construed as limitation. All temperatures are uncorrected.

EXAMPLE 1

The alkyl sulfonic acid hydrazides of formula III are prepared by the reaction of the corresponding sulfonic acid chloride with hydrazine hydrate analog as disclosed in Can. J. Chem. 33 (1955) 1250–55 (where $R_1$ is ethyl, n-propyl, isopropyl) and in accordance with Canadian Pat. No. 511,584 (for $R_1$=n-butyl, isobutyl and n-amyl). The compounds are oily-like, relatively unstable substances which are used in crude state as starting materials in the process of the invention.

Most of the alkyl sulfonic acid chlorides are prepared in accordance with J. Org. Chem. 16 (1951) 621–25. The isopropyl sulfochloride analog was prepared as described in Chem. Ber. 100 (1967) 1696–1700.

EXAMPLE 2

0.05 mol of o-formyl phenyl boric acid is dissolved in 100 ml of ethanol. While stirring, 0.05 mol of the selected alkyl sulfonyl hydrazide is added at room temperature. The temperature is slowly raised to boiling and after approximately 5 minutes of boiling, the reaction mixture is allowed to cool to 30° C. The mixture is evaporated and the residue stored at about 0° C., whereupon the desired products crystallize. On recrystallization from methanol, the product of formula I, wherein $R_4$ is hydrogen, is obtained in pure form.

In the table below, melting points (m.p.) and yields (in % of the theoretical yield) for compounds of formula I ($R_2$, $R_3$ and $R_4$=H) having different substituents for $R_1$ are shown:

| $R_1$ | m.p. in °C. | Yield |
|---|---|---|
| $C_2H_5-$ | 111-113 | 69.5 |
| $CH_3(CH_2)_2-$ | 84-85 | 38.1 |
| $CH_3$<br>    \\<br>      CH—<br>    /<br>$CH_3$ | 101-103 | 55.6 |
| $CH_3(CH_2)_3-$ | 48-49 | 53.0 |
| $CH_3$<br>    \\<br>      CH—CH$_2$—<br>    /<br>$CH_3$ | 62-63 | 53.4 |
| $CH_3-(CH_2)_4-$ | 51 | 43.5 |

EXAMPLE 3

The procedure is as described in Example 2. However, 0.05 mol of the selected alkenyl sulfonyl hydrazide, which is prepared in the same manner as described in Example 2, is used instead of the alkyl sulfonyl hydrazide.

The table below shows melting points, yields and solvents used in recrystallization of different compounds of formula I ($R_2$, $R_3$ and $R_4$=H) prepared in this way:

| $R_1$ | recrystallization solvent | m.p. in °C. | yield |
|---|---|---|---|
| $CH_2=CH-CH_2-$ | ethanol | 101-103 | 57 |
| $CH_2=C-CH_2-$<br>       \|<br>      $CH_3$ | acetone | 140-142 | 73.5 |

EXAMPLE 4

A mixture of 10 ml of hydrazine hydrate and 90 ml of ethanol is chilled to 0° C. and then, while stirring, a solution of 15 g of chloromethyl sulfonyl chloride in 10-15 ml of cold (0° C.) ethanol is added. The mixture is stirred for 30 minutes, the hydrazin-hydrochloride filtered off and the filtrate evaporated. The oily-like residue is dissolved in 25 ml of ethanol. This solution is added to a solution of 15 g o-formyl phenyl boric acid in 150 ml of ethanol. The further procedure is as described in Example 2. The 1-hydroxy-2-chloromethylsulfonyl-benzo-2,3,1-diazaborine thus obtained is recrystallized from ethanol and melts at 174°-175° C. The yield is 32% of the theoretical yield.

EXAMPLE 5

The procedure is as described in Example 2. However, 0.05 mol of the selected halogen alkyl sulfonyl hydrazide, which is prepared analog as described in Example 2, is used instead of the unsubstituted alkyl sulfonyl hydrazide used in Example 2.

The melting points and yields of the products obtained are shown in the following table: ($R_2$, $R_3$ and $R_4$=H)

| $R_1$ | m.p. in °C. | yield |
|---|---|---|
| $CH_3-CH-$<br>       \|<br>      Cl | 116-118° | 43.4% |
| $Cl-CH_2-CH_2-CH_2-$ | 102-104° | 57.0% |

EXAMPLE 6

5 g of 1-hydroxy-2-allylsulfonyl-benzo-2,3,1-diazaborine are suspended in 50 ml of absolute carbon tetrachloride. The flask is illuminated by using a 200-Watt lamp which is adjusted close to the wall of the flask, whereby the suspension becomes warm whereupon the suspended material dissolves. While stirring 3.5 g of bromine are introduced in vapor form, using a nitrogen stream to carry the bromine. Thereafter the illumination is continued for 30 minutes, during which time the nitrogen stream eliminates an excess of bromine from the reaction mixture. On chilling a precipitate deposites which is redissolved by adding chloroform. The solution is treated with silica gel, filtered and the filtrate is evaporated in a vacuum. The remaining oil is triturated with carbon tetrachloride which causes crystallization of 1-hydroxy-2-(2′,3′-dibromo-propylsulfonyl)-benzo-2,3,1-diazaborine.

Melting point: 112°-113° C.

Yield: 3 g=36.6% of the theoretical yield

EXAMPLE 7

The process is the same as described in Example 6, there are used, however, 3 g 1-hydroxy-2-allyl-sulfonyl-benzo-2,3,1-diazaborine, 30 ml carbon tetrachloride and about 1.6 g of chlorine. Thus the 1-hydroxy-2-(2′,3′-dichloro propylsulfonyl)-benzo-2,3,1-diazaborine melting at 102°-105° C. is obtained in a yield of 1.8 g=46.8% of the theoretical yield.

EXAMPLE 8

In a nitrogen atmosphere to a boiling solution of 0.4 g of anhydrous ferric chloride in 200 ml of dichloro methane there are added, while stirring, simultaneously over a period of 2 minutes solutions of 9 g of m-tolylaldehyde isobutylsulfonyl-hydrazone in 500 ml of dichloro methane and of 10 ml of boron tribromide in 30 ml of dichloro methane. The mixture is boiled under reflux for 5 minutes and then quickly cooled to about 0° to 5° C. The solution is poured into 300 ml ice water, the organic layer is separated and washed twice with 50 ml of water each. Thereafter the organic layer is extracted three times with 200 ml 1 normal sodium hydroxide solution each and the combined alkaline extracts are acidified with diluted hydrochloric acid. After extracting this acidic aqueous mixture with dichloro methane the organic extract is dried with magnesium sulfate and then evaporated in a vacuum. The remaining oil is dissolved in a small volume of warm ethanol. On chilling 1-hydroxy-2-isobutylsulfonyl-6-methyl-benzo-2,3,1-diazaborine crystallizes.

Melting point: 89°-90° C.

Yield: 33% of the theoretical.

EXAMPLE 9

The process is the same as described in Example 8, there are used, however, the n-propyl-sulfonyl-hydrazone of 3-fluoro benzaldehyde and boron tribromide to form the 1-hydroxy-2-(n-propylsulfonyl)-6-fluoro-benzo-2,3,1-diazaborine, which is purified by dissolving in one part of toluene and reprecipitating with three parts of petrol ether.

Melting point: 79°-81° C.

Yield: 55.6% of the theoretical

EXAMPLE 10

The procedure is the same as described in Example 8. However, the selected aldehyde-sulfonyl-hydrazone is used instead of m-tolylaldehyde isobutylsulfonyl-hydrazone. The table below shows melting points and yields of different compounds of formula I prepared in this way:

| formula | m.p. in °C | yield |
|---|---|---|
| (3-CH$_3$-benzo) OH–B–N–SO$_2$–CH$_2$–CH$_2$–CH$_2$–Cl, =N– | 128–130 | 50% |
| (3-C$_2$H$_5$-benzo) OH–B–N–SO$_2$–CH$_2$–CH$_2$–CH$_2$–Cl, =N– | 95–96 | 80.5% |
| (3-F-benzo) OH–B–N–SO$_2$–CH$_2$–CH$_2$–CH$_2$–Cl, =N– | 96–98 | 53% |
| (3,4-Cl$_2$-benzo) OH–B–N–SO$_2$–CH$_2$–CH$_2$–CH$_2$–Cl, =N– | 142–146 | 29% |
| (3-C$_2$H$_5$-benzo) OH–B–N–SO$_2$–CH$_2$–CH$_2$–CH$_3$, =N– | 75–77 | 58% |
| (3-C$_2$H$_3$-benzo) OH–B–N–SO$_2$–CH$_2$–CH(CH$_3$)–CH$_3$, =N– | 107–109 | 40% |

EXAMPLE 11

The procedure is the same as described in Example 8, there are used, however, the 3-chloropropylsulfonyl-hydrazone of 4-fluoro benzaldehyde and boron tribromide. The oily crude product obtained is dissolved in chloroform, treated with silica gel and filtered after standing for one hour. The filtrate is evaporated in a vacuum, the residue is suspended in water and admixed with 2 N sodium hydroxide solution until the mixture has a pH value of about 8 to 9. Undissolved particles are filtered off and then the filtrate is acidified with hydrochloric acid whereupon the 1-hydroxy-2-(3'-chloro-n-propylsulfonyl)-7-fluoro-benzo-2,3,1-diazaborin is precipitated which finally is recrystallized from ethanol.

Melting point: 115°–117° C.
Yield: 30.5% of the theoretical.

EXAMPLE 12

0.05 mol of a compound of formula I ($R_4$=hydrogen), as for instance, 12.5 g of 1-hydroxy-2-allyl-sulfonyl-benzo-2,3,1-diazaborine, is added at room temperature, while stirring, to 100 ml of water. There is added 2 N-sodium hydroxide solution until the pH is 7 whereupon a solution is obtained which is filtered. The filtrate on lyophilization gives the sodium salt of the benzo-2,3,1-diazaborine derivative used, in form of a white powder which is easily soluble in water.

Following the procedures as described in the examples as supplemented by the description, the 1-hydroxy-benzo-2,3,1-diazaborine derivatives having the following substituents in the 2-position of the ring are obtained.

| R—SO$_2$— | R—SO$_2$— |
|---|---|
| bromo methyl sulfonyl | (Br—CH$_2$—SO$_2$—) |
| dichloro methyl sulfonyl | (Cl$_2$—CH—SO$_2$—) |
| trifluoro methyl sulfonyl | (CF$_3$—SO$_2$—) |
| trichloro methyl sulfonyl | (CCl$_3$—SO$_2$—) |
| vinyl sulfonyl | (CH$_2$=CH—SO$_2$—) |
| 2-chloro ethyl sulfonyl | (Cl—CH$_2$—CH$_2$—SO$_2$—) |
| 1,2-dichloro ethyl sulfonyl | (Cl—CH$_2$—CH(Cl)—SO$_2$—) |
| 1,2-dibromo ethyl sulfonyl | (Br—CH$_2$—CH(Br)—SO$_2$—) |

-continued

| R—SO₂— | R—SO₂— |
|---|---|
| 2,2-dichloro ethyl sulfonyl | (Cl₂—CH—CH₂—SO₂—) |
| 2,2,2-trifluoro ethyl sulfonyl | (CF₃—CH₂—SO₂—) |
| crotyl sulfonyl | (CH₃—CH=CH—SO₂—) |
| 1,3-dichloro propyl sulfonyl | (ClCH₂—CH₂—CH—SO₂—<br>                               Cl |
| 1,2,3-trichloro propyl sulfonyl | (ClCH₂CH—CH—SO₂—)<br>             Cl  Cl |
| buten-(1)-yl sulfonyl | (CH₃—CH₂—CH=CH—SO₂—) |
| buten-(2)-yl sulfonyl | (CH₃—CH=CH—CH₂—SO₂—) |
| buten-(3)-yl sulfonyl | (CH₂=CH—CH₂—CH₂—SO₂—) |
| 2-methyl-propen-(1)-yl sulfonyl | (CH₃—C=CH—SO₂—)<br>            CH₃ |
| penten-(1)-yl sulfonyl | (CH₃—CH₂—CH₂—CH=CH—SO₂—) |
| penten-(2)-yl sulfonyl | (CH₃—CH₂—CH=CH—CH₂—SO₂—) |

In the 1-hydroxy-benzo-2,3,1-diazaborine derivatives having the substituents in the 2-position of the ring mentioned before the benzene ring may be unsubstituted or substituted by substituents as defined for $R_2$ and $R_3$. Thus following the procedures described in the examples for instance also the following compounds of formula I can be obtained:

1-hydroxy-2-allylsulfonyl-6-methyl-benzo-2,3,1-diazaborine 1-hydroxy-2-(3'-bromo-n-propyl-sulfonyl)-6-methyl-benzo-2,3,1-diazaborine 1-hydroxy-2-(3'-chloro-n-propylsulfonyl)-5,7-dimethyl-benzo-2,3,1-diazaborine 1-hydroxy-2-(α-chloroäthylsulfonyl)-6-methyl-benzo-2,3,1-diazaborine 1-hydroxy-2-(iso-butylsulfonyl)-6-fluoro-benzo-2,3,1-diazaborine 1-hydroxy-2-(crotylsulfonyl)-6-methyl-benzo-2,3,1-diazaborine 1-hydroxy-2-(vinylsulfonyl)-6-ethyl-benzo-2,3,1-diazaborine 1-hydroxy-2-(methallylsulfonyl)-6-methyl-benzo-2,3,1-diazaborine 1-hydroxy-2-(isobutylsulfonyl)-6-chloro-benzo-2,3,1-diazaborine 1-hydroxy-2-(3'-chloro-n-propylsulfonyl)-6-propyl-benzo-2,3,1-diazoborine 1-hydroxy-2-(3-propylsulfonyl)-6-butyl-benzo-2,3,1-diazaborine and other compounds of formula I and their salts with pharmaceutically acceptable bases.

The new compounds of formula I of the invention possess, as described above, high activity against gram-negative bacteria. It is also noteworthy that the compounds of the invention exhibit also low toxicity and hence are very well suited for therapy or control of gram-negative infections in warm-blooded mammals such as man and animals. They can be administered orally, parenterally, topically or rectally. The low toxicity of the compounds of the invention is even evident on prolonged administration and they do not produce adverse side effects.

Regarding the antimicrobial compositions of the invention they can be prepared and administered in accordance with well accepted medical and pharmaceutical practices. For oral administration they can be made up into powders, tablets or other solid state preparations. They can also be used in aqueous or saline suspensions or solutions for parenteral administration like intramuscular injection or other aqueous solutions, particularly those in which $R_4$ is an alkaline metal, which salts are water soluble.

Since other aspects of the preparation and administration of the pharmaceutical compositions incorporating the compounds of the invention are known from prior literature, reference is made herein again to U.S. Pat. No. 3,714,206, particularly those sections dealing with pharmaceutical compositions of columns 26 and 27 and others, which are incorporated herein by reference. Conveniently, the compositions of the invention contain from 1% to about 100% by weight of the total weight of the composition, of the effective compound of formula I of the invention.

The new compounds have proved to be especially valuable for topical administration as antimicrobial agents, for instance, in the form of salves, ointments, creams, pastes, cerates, plasmas, liniments, dusting powders, emulsions, lotions, and the like topically applicable compositions. Incorporation of the compounds into adhesive plasters and tapes, especially those provided with pads such as the so-called "Band-Aids" and the like is also possible. They may be incorporated in soaps and other detergents, if desired, in combination with other active agents, for instance, with antibacterial agents which are effective against gram-positive bacteria. Rectal or vaginal administration, for instance, in the form of rectal and vaginal suppositories or urethral bougies whereby the vehicle may be cocoa butter (theobroma oil), glycerinated gelatin, mixtures of polyethylene glycols, or other conventionally used suppositories is also possible.

These and other pharmaceutical compositions are prepared in a manner known per se and with pharmaceutical incipients as they are conventionally used for this purpose. It may be mentioned that the new compounds and their pharmaceutical compositions have proved of value not only in human medicine but also in veterinary medicine.

The compositions of the invention are prepared as shown in the examples of U.S. Pat. No. 3,714,206.

We claim:

1. A 1-hydroxy-benzo-2,3,1-diazaborine of the formula

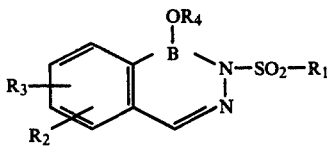

in which
- R₁ is a radical selected from the group consisting of acyclic alkyl and alkenyl radicals having 2 to 5 carbon atoms and such radicals substituted with from 1 to 3 halogen atoms, and mono-, di-, and tri-halogen methyl radicals,
- R₂ and R₃ are the same or different substituents selected from the group consisting of $C_1$ and $C_4$ alkyl radicals and hydrogen, fluorine, chlorine and bromine atoms, with the proviso that only one of the substituents may be hydrogen, and
- R₄ is a substituent selected from the group consisting of hydrogen and cations which provide a pharmaceutically acceptable material effective to control gram-negative bacteria.

2. The compound of claim 1 in which neither R₂ or R₃ is hydrogen.

3. The compound of claim 2 in which R₂ and R₃ are methyl.

4. The compound of claim 2 in which R₂ and R₃ are chlorine.

5. The compound of claim 1 in which R₁ is straight chain.

6. The compound of claim 5 in which the halogen of R₁ is chlorine.

7. The compound of claim 1 in which R₁ is branched chain.

8. The compound of claim 7 in which the halogen of R₁ is chlorine.

9. The compound of claim 1 in which R₁ is an alkenyl radical having 3 to 5 carbon atoms with the double bond between the 2- and 3- carbon atoms.

10. The compound of claim 1 in which R₁ has 3 to 4 carbon atoms.

11. The compound of claim 10 in which R₁ has a single chlorine substituent.

12. The compound of claim 1 in which R₁ is a 1 to 3 carbon atom haloalkyl radical substituted by 1 to 3 halogen atoms.

13. The compound of claim 12 in which the haloalkyl radical is monochloralkyl.

14. The compound of claim 1 in which R₃ is hydrogen and R₂ is attached to the 6-position of the benzo-2,3,1-diazaborin and represents a member of the group consisting of $C_1$ to $C_4$ alkyl and a fluorine, chlorine or bromine atom.

15. The compound of claim 14 in which R₂ is methyl.

16. The compound of claim 14 in which R₂ is ethyl.

17. The compound of claim 14 in which R₂ is fluorine.

18. The compound of claim 14, 1-hydroxy-2-(n-propylsulfonyl)-6-fluoro-benzo-2,3,1-diazaborine or a non-toxic pharmaceutically acceptable salt thereof.

19. The compound of claim 14, 1-hydroxy-2-(3'-chloro-n-propylsulfonyl)-6-methyl-benzo-2,3,1-diazaborine or a non-toxic pharmaceutically acceptable salt thereof.

20. The compound of claim 14, 1-hydroxy-2-(3'-chloro-n-propylsulfonyl)-6-ethyl-benzo-2,3,1-diazaborine or a non-toxic pharmaceutically acceptable salt thereof.

21. The compound of claim 14, 1-hydroxy-2-(3'chloro-n-propylsulfonyl)-6-fluoro-benzo-2,3,1-diazaborine or a non-toxic pharmaceutically acceptable salt thereof.

22. The compound of claim 14, 1-hydroxy-2-(isobutylsulfonyl)-6-methyl-benzo-2,3,1-diazaborine or a non-toxic pharmaceutically acceptable salt thereof.

23. The compound of claim 14, 1-hydroxy-2-(n-propylsulfonyl)-6-ethyl-benzo-2,3,1-diazaborine or a non-toxic pharmaceutically acceptable salt thereof.

24. A pharmaceutical composition which comprises an effective amount for controlling gram-negative bacteria of a compound of claim 1, in combination with a pharmaceutically acceptable carrier.

25. The composition of claim 24 in which R₁ is chlorine-substituted.

26. The composition of claim 24 in which R₄ is an alkali metal cation.

27. The composition of claim 24 in which the pharmaceutically active compound is a water-soluble salt.

28. The composition of claim 24 in which the carrier is water.

29. A process of controlling gram-negative bacterial infections in warm-blooded mammals which comprises administering to the mammal a therapeutically effective amount of a 1-hydroxybenzo-2,3,1-diazaborine derivative of claim 1, or a pharmaceutically acceptable water-soluble salt thereof, in combination with a pharmaceutically acceptable carrier.

30. The composition of claim 24 in which the compound is defined in any one of claims 18, 19, 20, 21, 22, or 23.

* * * * *